(12) United States Patent
Tatinclaux (10) Patent No.: US 8,836,498 B2
(45) Date of Patent: Sep. 16, 2014

(54) OCCUPANT SUPPORT WITH AN EXTENDED FUNCTIONALITY OCCUPANT POSITION MONITORING SYSTEM

(71) Applicant: Philippe Tatinclaux, Chevry (FR)

(72) Inventor: Philippe Tatinclaux, Chevry (FR)

(73) Assignee: Hill-Rom Services, Inc., Batesville, IN (US)

( * ) Notice: Subject to any disclaimer, the term of this patent is extended or adjusted under 35 U.S.C. 154(b) by 54 days.

(21) Appl. No.: 13/754,244

(22) Filed: Jan. 30, 2013

(65) Prior Publication Data

US 2014/0210610 A1 Jul. 31, 2014

Related U.S. Application Data

(60) Provisional application No. 61/757,885, filed on Jan. 29, 2013.

(51) Int. Cl.
*G08B 23/00* (2006.01)

(52) U.S. Cl.
CPC ... *G08B 23/00* (2013.01); *Y10S 5/94* (2013.01)
USPC ........ 340/501; 340/524; 340/666; 340/691.1; 340/691.8; 5/940

(58) Field of Classification Search
USPC .............. 340/501, 286.07, 573.1, 573.4, 524, 340/540, 666, 667, 686.1, 691.1, 691.8, 3.7, 340/3.71; 5/658, 904, 905, 940
See application file for complete search history.

(56) References Cited

U.S. PATENT DOCUMENTS

| | | | |
|---|---|---|---|
| 5,279,010 A | 1/1994 | Ferrand et al. | |
| 6,208,250 B1 | 3/2001 | Dixon et al. | |
| 7,461,425 B2 | 12/2008 | Chambers et al. | |
| 7,746,218 B2 * | 6/2010 | Collins et al. | 340/286.07 |
| 8,593,284 B2 * | 11/2013 | Tallent et al. | 340/573.1 |
| 2005/0219059 A1 * | 10/2005 | Ulrich et al. | 340/686.1 |

* cited by examiner

*Primary Examiner* — Toan N Pham
(74) *Attorney, Agent, or Firm* — Kenneth C. Baran (57) ABSTRACT

An occupant support comprises an occupant support structure which includes an occupant position monitoring system comprising a sensor for producing a sensor output signal as a function of occupant position on the occupant support structure, and an alarm state selector for enabling or disabling an alarm. A controller receives the sensor output signal and produces a controller output signal for commanding the alarm and a nonalarm device such that such that when the alarm is disabled the controller output signal governs operation of the nonalarm device but not operation of the alarm device and when the alarm is enabled the controller output signal governs operation of the nonalarm device and the alarm device.

18 Claims, 8 Drawing Sheets

| Occupant Position Monitor (PPM) State | Alarm State | Row | Occupant Position Monitor (PPM) Status | Response | | | |
|---|---|---|---|---|---|---|---|
| | | | | Alarm | Nonalarm Device | | |
| | | | | | Lighting | | Timer |
| Armed/ON (default) | Disabled (OFF) | A | Triggered | Dormant | ON or Increase | | Change Mode |
| | | B | Not Triggered | Dormant | Manual | | None |
| | | C | Reset | Dormant | Remain ON or revert | | Change Mode |
| | Enabled (ON) | D | Triggered | Operational/alarming | ON or Increase | | Change Mode |
| | | E | Not Triggered | Operational/not alarming | Manual | | None |
| | | F | Reset | Operational | Remain ON or revert | | Change Mode |
| Not Armed /OFF | Disabled (OFF) | G | Triggered | Dormant | None | | None |
| | | H | Not Triggered | Dormant | None | | None |
| | | I | Reset | Dormant | None | | None |
| | Enabled (ON) | J | Triggered | Dormant | None | | None |
| | | K | Not Triggered | Dormant | None | | None |
| | | L | Reset | Dormant | None | | None |

FIG. 5A

| Occupant Position Monitor (PPM) State | Alarm State | Row | Occupant Position Monitor (PPM) Status | Response Alarm | Response Nonalarm Device Lighting | Response Nonalarm Device Timer |
|---|---|---|---|---|---|---|
| Armed/ON (default) | Disabled (OFF) | A | Triggered | Dormant | ON or Increase | Change Mode |
| | | B | Not Triggered | Dormant | Manual | None |
| | | C | Reset | Dormant | Remain ON or revert | Change Mode |
| | Enabled (ON) | D | Triggered | Operational/alarming | ON or Increase | Change Mode |
| | | E | Not Triggered | Operational/not alarming | Manual | None |
| | | F | Reset | Operational | Remain ON or revert | Change Mode |

FIG. 5B

| Alarm State | Row | Occupant Position Monitor (PPM) Status | Response | | |
|---|---|---|---|---|---|
| | | | Alarm | Nonalarm Device | |
| | | | | Lighting | Timer |
| Disabled (OFF) | A | Triggered | Dormant | ON or Increase | Change Mode |
| | B | Not Triggered | Dormant | Manual | None |
| | C | Reset | Dormant | Remain ON or revert | Change Mode |
| Enabled (ON) | D | Triggered | Operational/alarming | ON or Increase | Change Mode |
| | E | Not Triggered | Operational/not alarming | Manual | None |
| | F | Reset | Operational | Remain ON or revert | Change Mode |

FIG. 5C

|  | Occupant Position Monitor Status | Is occupant in bed or out of bed? | Light state (example 1) | Light state (example 2) |
|---|---|---|---|---|
| Time |  |  |  |  |
| $t_0$ | Not triggered | In | Off | Off |
| $t_1$ | Triggered | Out | On | On |
| $t_2$ | Not triggered | In | Remain on | Revert to off |
| $t_3$ | Triggered | Out | Remain on | On or revert to on |
| ⋮ | ⋮ | ⋮ | ⋮ | ⋮ |

FIG. 6

| Time interval | Time | Occupant Position Monitor Status | Is occupant in bed or out of bed? | In bed timer mode (example 1) | Out of bed timer mode (example 2) | Timer mode (example 3) | |
|---|---|---|---|---|---|---|---|
|  |  |  |  |  |  | "In bed" timer | "Out of bed" timer |
| $\Delta t_A$ | $t_0$ | Not triggered | In | Start (operating) | Stop (not operating) | Start |  |
| $\Delta t_B$ | $t_1$ | Triggered | Out | Stop (not operating) | Start (operating) | Stop (not oper.) | Start (operating) |
| $\Delta t_C$ | $t_2$ | Not triggered | In | Start (operating) | Stop (not operating) | Start (operating) | Stop (not oper.) |
|  | $t_3$ | Triggered | Out | Stop (not operating) | Start (operating) | Stop (not oper.) | Start (operating) |
|  | ⋮ | ⋮ | ⋮ | ⋮ | ⋮ | ⋮ | ⋮ |

OCCUPANT SUPPORT WITH AN EXTENDED FUNCTIONALITY OCCUPANT POSITION MONITORING SYSTEM

TECHNICAL FIELD

The subject matter described herein relates to occupant supports, such as a hospital bed, having a monitoring system for monitoring the position of an occupant of the occupant support and in which the monitoring system is armed by default and a controller responds to occupant position by governing operation of a nonalarm device but not operation of an alarm.

BACKGROUND

Certain hospital beds include an occupant position monitoring system, also known as a patient position monitoring system or PPM system. An example PPM system is described in U.S. Pat. No. 6,208,250, the contents of which are incorporated herein by reference. The system disclosed in U.S. Pat. No. 6,208,250 has three levels of sensitivity which can be selected by a user, usually a caregiver. When the PPM system is armed, it activates an alarm if the position of the patient violates position criteria associated with the selected sensitivity level. The lowest sensitivity setting results in activation of the alarm only if the occupant actually exits the bed. A moderate sensitivity setting results in activation of the alarm if the occupant assumes a position on the bed consistent with an intent to exit. The most sensitive sensitivity setting results in activation of the alarm if the occupant merely moves away from a defined position on the bed, for example if the occupant migrates laterally away from the center of the bed and toward the left or right edge of the bed by more than an acceptable amount, or if the occupant sits up from a lying position. If the occupant is under no restrictions as to his or her movement, including being cleared to exit the bed without assistance or supervision, the caregiver may disarm the system, in which case the alarm remains inactive irrespective of occupant position.

The described system is useful for monitoring and regulating movement of patients whose movement and/or position on the bed needs to be restricted. However the functionality of the system cannot reasonably be extended. For example if the system were modified to command devices or functions other than the alarm (referred to herein as nonalarm devices or functions) in response to the movement and/or position of an occupant who is under no restrictions as to his or her movement and/or position, the modified system would also unnecessarily activate the alarm.

Accordingly, a solution is sought to the problem of extending the use of a PPM system to command nonalarm devices and/or functions without activating the alarm.

SUMMARY

An occupant support comprises an occupant support structure which includes an occupant position monitoring system comprising a sensor for producing a sensor output signal as a function of occupant position on the occupant support structure, and an alarm state selector for enabling or disabling an alarm. A controller receives the sensor output signal and produces a controller output signal for commanding the alarm and a nonalarm device such that when the alarm is disabled the controller output signal governs operation of the nonalarm device but not operation of the alarm device and when the alarm is enabled the controller output signal governs operation of the nonalarm device and the alarm device.

BRIEF DESCRIPTION OF THE DRAWINGS

The foregoing and other features of the various embodiments of the occupant support described herein will become more apparent from the following detailed description and the accompanying drawings in which.

DETAILED DESCRIPTION

Figure 1:
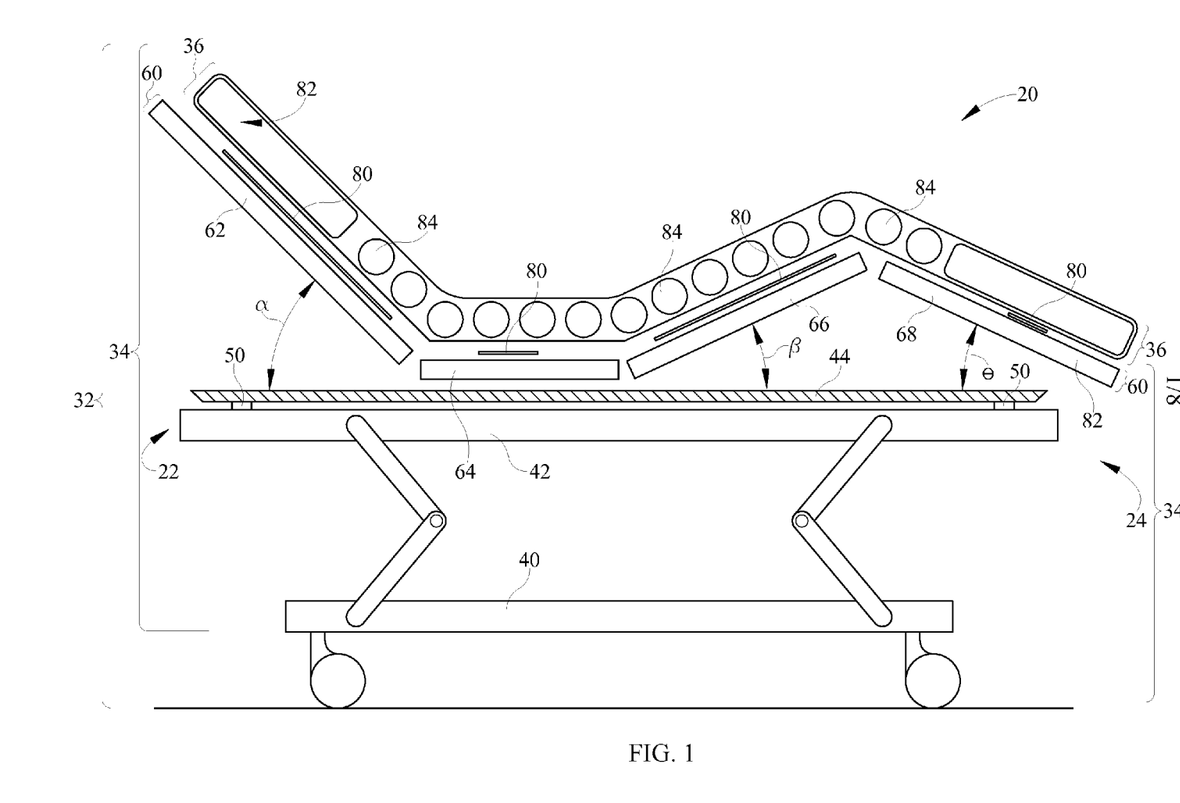
FIG. 1 is a schematic side elevation view of a hospital bed.
Figure 2:
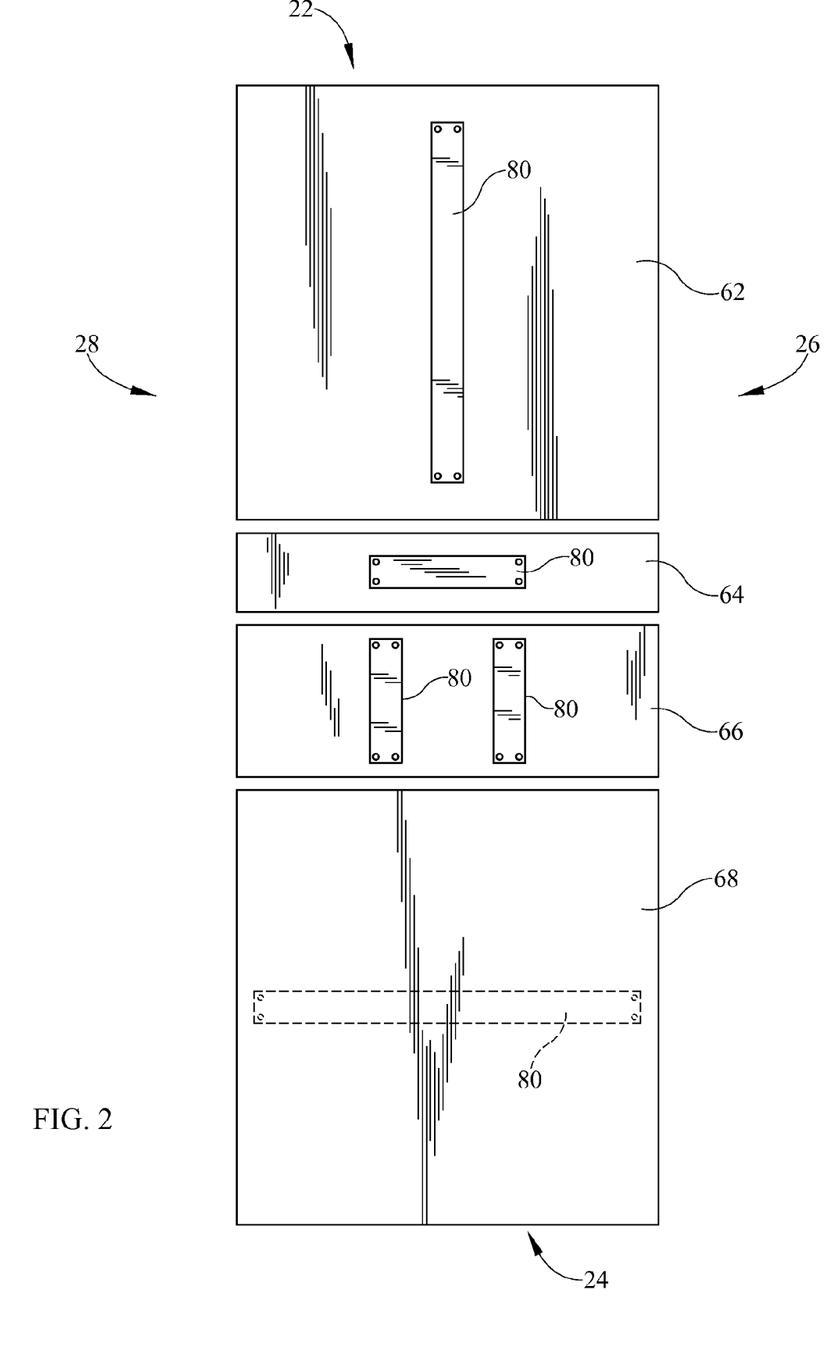
FIG. 2 is a plan view of a deck component of the bed of FIG. 1
Figures 3, 4:
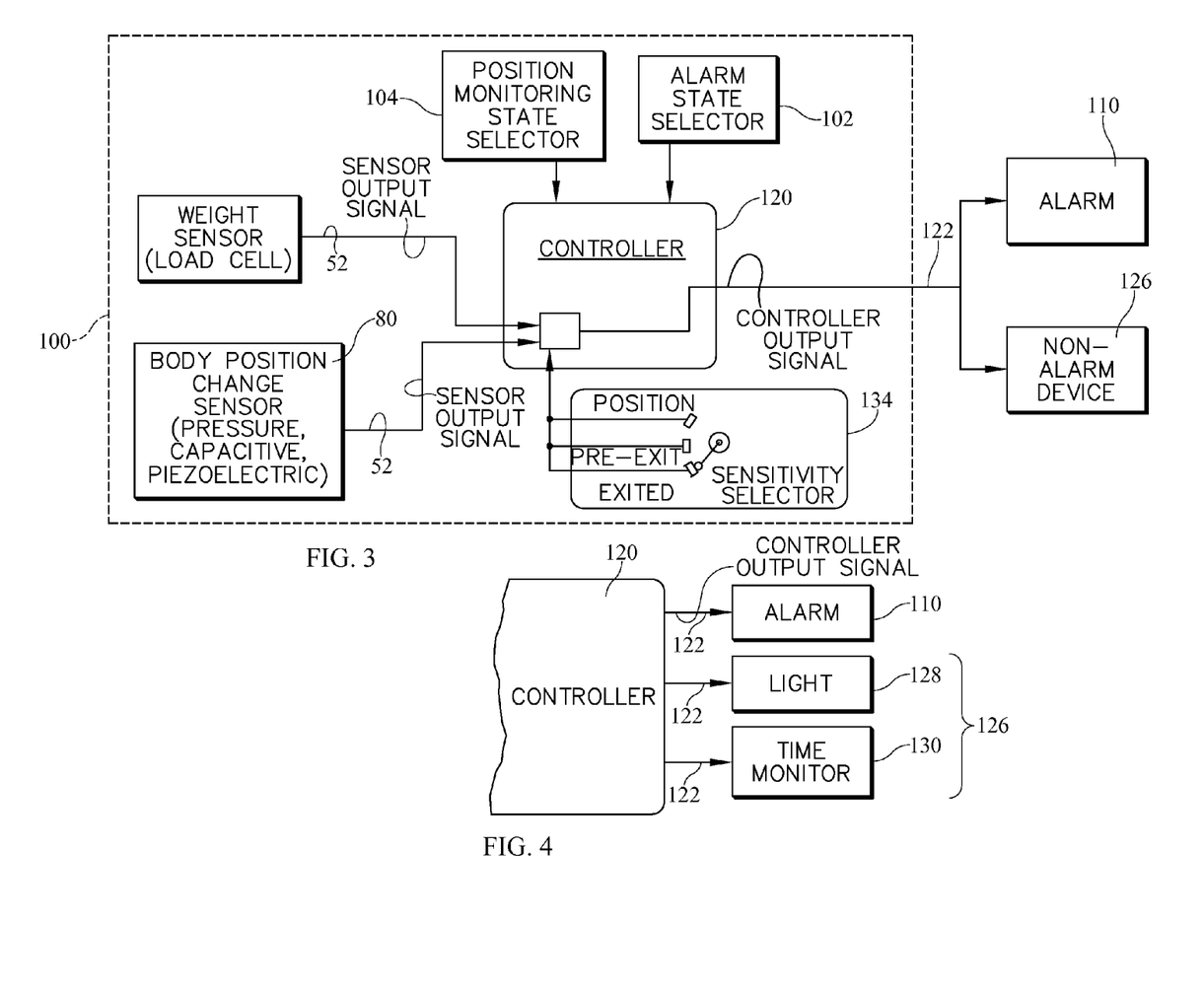
FIG. 3 is a block diagram showing an occupant position monitoring system, an alarm, a nonalarm device, and a controller output signal from a controller to the alarm and the nonalarm device.
FIG. 4 is a fragmentary view of the controller of FIG. 3 showing individual output signals and showing a light and a time monitor as examples of a nonalarm device.

Referring to FIGS. 1-3, an occupant support exemplified as hospital bed 20 extends longitudinally from a head end 22 to a foot end 24 and laterally from a left side 26 to a right side 28. The bed comprises an occupant support structure 32 which includes a framework 34 and a mattress 36. The framework includes a base frame 40, and an intermediate frame 42 mounted on the base frame such that the intermediate frame can be raised or lowered in elevation relative to the base frame. The framework also includes a weigh frame 44 mounted on the intermediate frame such that the load path from the weigh frame to the intermediate frame extends through a first sensor or set of sensors which may be weight sensors such as load cells 50 located near each of the four corners of the weigh frame. The load cells enable measurement of the weight of an occupant of the bed and, as a result, produce a sensor output signal 52 which is responsive to changes in weight applied to the occupant support structure and therefore indicative of the position of an occupant on the occupant support structure. The occupant support also includes a segmented deck 60 comprising an upper body section 62 corresponding approximately to the occupant's torso, a seat section 64 corresponding approximately to the occupant's buttocks, a thigh section 66 corresponding approximately to the occupant's thighs, and a calf section 68 corresponding approximately to the occupant's calves and feet. The angular orientations $\alpha$, $\beta$, $\theta$ of the upper body, thigh and calf sections are adjustable. A second sensor 80 or set of sensors is fastened to the deck sections. Illustratively, sensors

80, are resistive pressure sensors. Other types of sensors may be used instead. For example, capacitance sensors such as shown in U.S. Pat. No. 5,808,552 or in U.S. Pat. No. 6,067,019 or a piezoelectric sensor such as disclosed in co-pending U.S. Pat. No. 6,252,512 may be used. In another embodiment, sensors 80 are coupled to a top or bottom surface of mattress 36 or are located within an interior region of the mattress. The second set of sensors 80, like first set of sensors 50 produces one or more sensor output signals 52 responsive to and therefore indicative of occupant position on the occupant support structure.

Mattress 36 may be made of foam 82 or other cushioning material. Alternatively, the mattress may comprise air bladders 84 whose firmness can be adjusted by introducing air into the bladders or by venting air from the bladders. The illustrated mattress is a combination foam and bladder mattress.

The occupant support also includes an occupant position monitoring system 100, also referred to as a patient position monitoring system or simply a PPM system. An example position monitoring system is described in U.S. Pat. No. 6,208,250, the contents of which are incorporated herein by reference.

The occupant support also includes an alarm state selector 102 for enabling or disabling an alarm 110. The alarm may be a local alarm device mounted on the occupant support. Alternatively the alarm may be located somewhere other than on the occupant support, for example on a wall of the room or at a nurses' station, in which case the alarm would not be considered part of the occupant support. The default state of the alarm is the disabled state.

The occupant support may or may not include a position monitoring state selector 104 for changing the state of the position monitoring system. If selector 104 is provided, the default state of the position monitoring system is the armed state, so that the selector is an override selector for overriding the armed default state of the position monitoring system and placing it in a disarmed state. If selector 104 is not provided, the only state available for the position monitoring system is a state analogous to the armed state. Such a state will be referred to herein as the armed or default state even though no other state is available for the position monitoring system to be placed in. In the interest of generality, the remainder of this specification assumes the existence of selector 104 unless the context or an explicit statement indicates otherwise.

Referring additionally to FIG. 4, the occupant support also includes a controller 120 configured to receive sensor output signal 52 and to produce a controller output signal or command 122 for commanding alarm 110 and a nonalarm device 126, for example a light 128 or a time monitor 130 such as a clock or timer, such that when the monitoring system is armed and the alarm is disabled the controller output signal governs operation of the nonalarm device but not operation of the alarm device, and when the monitoring system is armed and the alarm is enabled the controller output signal governs operation of the nonalarm device and the alarm device. In one embodiment, when the monitoring system is disarmed the controller does not govern operation of the alarm and does not govern operation of the nonalarm device irrespective of whether the alarm is enabled or disabled.

FIG. 3 shows controller output signal 122 as a single signal delivered to both the alarm device and to the non-alarm device. FIG. 4 shows controller output signal 122 as a set of individual signals.

"Alarm" means a human perceivable stimulus or a device for generating such a stimulus, the stimulus intended to capture the attention of a person despite the possible presence of distractions and advise of a condition requiring the attention or intervention of the person. An alarm need not indicate an emergency condition requiring immediate action, for example action to prevent loss of life, injury or significant property loss. However an alarm does indicate a condition requiring attention without undue delay. By contrast, conditions which do not qualify as an alarm include routine status reports and/or updates, "information only" reports, routine collection of data, or routine reminders.

"Operation of the alarm device" and similar phrases means activating or increasing the alert level of the alarm in response to the existence or absence of prescribed conditions and may include deactivating (or decreasing the alert level) of a previously activated alarm or otherwise changing the operational state of the alarm.

"Operation of the nonalarm device" and similar phrases means affecting the state of the device in response to the existence or absence of prescribed conditions. In one example the nonalarm device is a light 128 that can be set to higher and lower illumination settings (one or both of which can be "on" and "off" respectively), the prescribed condition is detection of conditions consistent with a bed occupant having exited the bed, and affecting the state of the light is manifested by the light being set to the higher illumination level (if not already at that level). In another example the nonalarm device is a time monitor 130 (e.g. a clock or timer and associated memory), the prescribed condition is detection of conditions consistent with a bed occupant having exited the bed, and affecting the state of the time monitor is manifested by the monitor being activated to record the time of day at which the occupant exited the bed.

"Governing operation" and similar phrases means that at least two options exist and the controller is configured to select one of the at least two options. By contrast when all the choices available to the controller are the same, the controller is not governing operation of the alarm device or nonalarm device in question.

The occupant support also includes a user operable sensitivity selector 134 for selecting among at least two occupant position monitoring sensitivity settings. The specific embodiment of FIG. 3 has exactly three occupant position monitoring sensitivity settings. These settings are an EXITED setting, a PRE-EXIT setting and a POSITION setting. If a user selects the EXITED setting (the setting illustrated), he or she causes the occupant position monitoring system to be triggered if the controller perceives that the occupant has exited the occupant support. If a user selects the PRE-EXIT setting, he or she causes the occupant position monitoring system to be triggered if the controller perceives that the occupant is in a position suggestive of an intent to exit the occupant support. If a user selects the POSITION setting, he or she causes the occupant position monitoring system to be triggered if the controller perceives that the occupant is in an unsatisfactory or unauthorized position other than the position suggestive of an intent to exit the occupant support. Accordingly, controller output signal 122 is a function of the sensitivity setting. In another embodiment of the occupant support the sensitivity selector is not present. Instead, the occupant position monitoring system is designed to be sensitive to only a single prescribed positioning constraint, e.g. the "EXITED" constraint.

In one embodiment controller 120 is configured so that output signal 122 is an "EXITED" output signal that corresponds to an occupant having exited the occupant support, and so that at least one other output signal 122 corresponds to the occupant having not exited the occupant support. In another embodiment the controller is configured so that the at least one other controller output signal 122 is a "PRE-EXIT"

signal corresponding to an occupant being in a position suggestive of an intent to exit the occupant support and a "POSITION" signal corresponding to an occupant being in an unsatisfactory or unauthorized position on the occupant support other than the position suggestive of an intent to exit the occupant support.

Figure 5A:
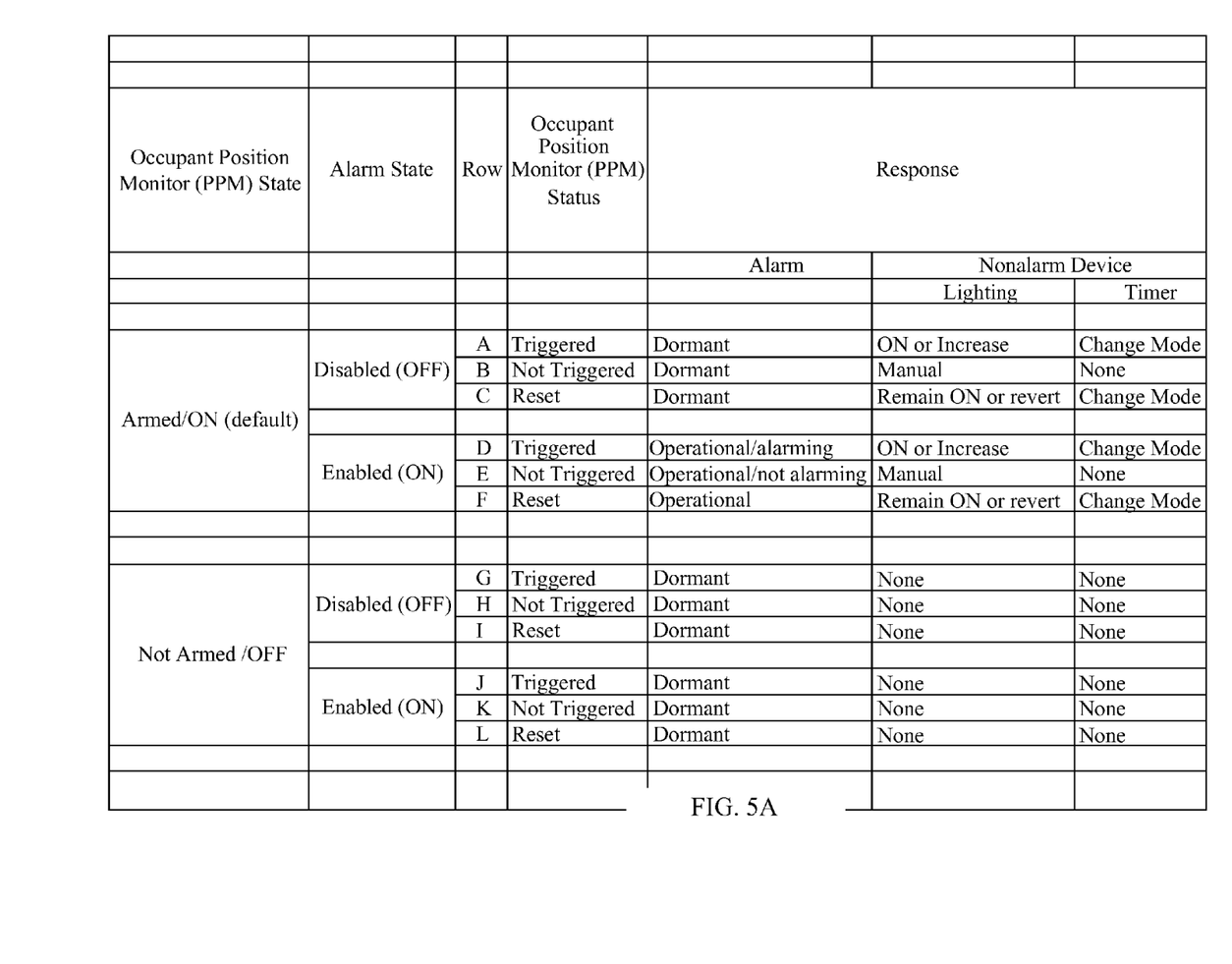
FIGS. 5A-5C are tables showing the response of the alarm device and nonalarm device of FIG. 3 as a function of the state of the position monitoring system, the state of the alarm, and the status of the occupant position monitor (FIG. 5A) and showing response as a function of the state of the alarm and the status of the occupant position monitor (FIGS. 5B-5C).

FIG. 5A is a table showing the response of alarm device 110 and nonalarm device 126 as a function of the state of the position monitoring system (armed or not armed), the state of the alarm (enabled or disabled) and the status of the occupant position monitor. Row codes A through L are used to identify specific combinations of position monitor state, alarm state and occupant position monitor status. The status of the occupant position monitor (as distinct from its state, which refers to whether the system is armed or disarmed) refers to whether or not the occupant's position violates the prescribed position constraints of whichever sensitivity setting a user has selected (e.g. EXITED, PRE-EXIT or POSITION). As already noted the occupant position monitoring system is considered to have been triggered if 1) the EXITED setting has been selected and the controller perceives that the occupant has exited the occupant support, 2) the PRE-EXIT setting has been selected and the controller perceives that the occupant is in a position suggestive of an intent to exit the occupant support or 3) the POSITION setting has been selected and the controller perceives that the occupant is in an unsatisfactory or unauthorized position other than the position suggestive of an intent to exit the occupant support.

The following examples are for the case where a user has selected the "EXITED" sensitivity setting. Operation at other sensitivity settings is the same except, of course, for the conditions that cause the occupant position monitoring status to be "TRIGGERED" or "NOT TRIGGERED".

Continuing to refer to FIG. 5A, if the occupant position monitor is armed, which is its default state, the alarm is disabled (which is the default state of the alarm), and the position monitor status is "TRIGGERED", (Row A) the alarm remains dormant and controller output signal 122 affects a nonalarm device, such as a light or timer. In the case where the nonalarm device is a light, the output signal 122 causes a light to turn on (assuming the light had not already be on) or causes a light which had been operating at a low level of illumination intensity to operate at a higher level of intensity. For simplicity, the balance of this specification will use only the off/on example rather than the low intensity/high intensity example. The light in question may be, but is not limited to, a night light, a room light in the room, a room light in a nearby bathroom, lights embedded in the room floor to indicate a path from the bed to another location such as the bathroom, or some combination thereof. In the case where the nonalarm device is a time monitor, the output signal 122 causes a change in the operating mode of the timer, for example to start or to stop.

Continuing to refer to FIG. 5A, row B shows the case where the occupant position monitor is in its armed, default state, the alarm is disabled (its default state), and the position monitor status is "NOT TRIGGERED". Under those conditions the alarm remains dormant. The light remains in a manual mode of operation, i.e. output signal 122 does not automatically turn the light on, but instead leaves the light in a state in which it must be operated manually or by some means other than by signal 122. Similarly signal 122 does not affect the timer. Instead the timer continues operating as it had been.

Figure 6:
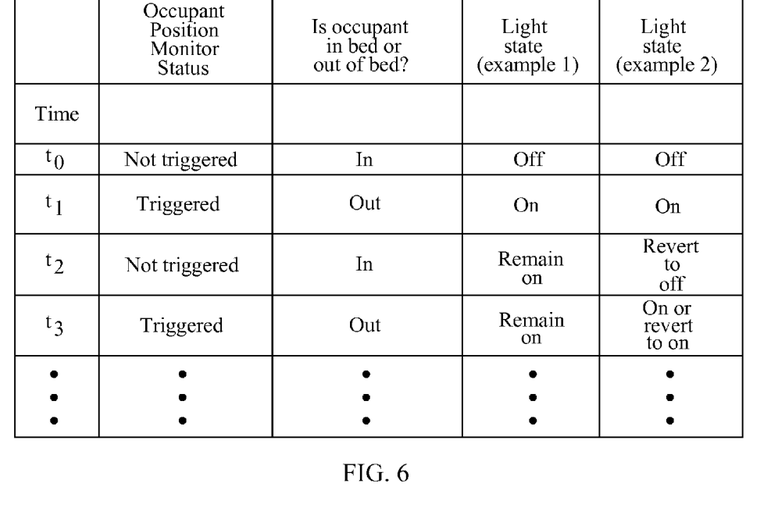
FIG. 6 is a table showing two examples of operation of a light as a function of the status of the position monitoring system.

Continuing to consider the case where the occupant position monitor is in its armed, default state and the alarm is disabled, FIG. 5A also accounts for a position monitor status referred to as "RESET" (row C). The "RESET" status refers to a sequence of events in which the position monitor status changes from "TRIGGERED" to "NOT TRIGGERED", and back to "TRIGGERED" or vice versa ("NOT TRIGGERED" to "TRIGGERED", and back to "NOT TRIGGERED"). As before, the alarm remains dormant. Referring additionally to FIG. 6, the light, if already on, remains on. This is seen in FIG. 6, example 1, event sequence t1 to t1 to t2 where the light, which was on at t1 as a result of the occupant position monitor status of "TRIGGERED", remains on after the monitor status returns to "NOT TRIGGERED" at t2. The same outcome arises from example 1 event sequence t1 to t2 to t3 where the light, which was on at t2, remains on after the monitor status returns to "TRIGGERED" at t3.). Alternatively, the system may be arranged so that controller output signal 122 causes the light to revert to its previous operating condition. This is seen in FIG. 6, example 2, event sequence t0, t1, t2 where the position monitor status has changed from "NOT TRIGGERED" to "TRIGGERED" at t1, and back to "NOT TRIGGERED" at t2. At t1, the light, which had previously been off, has been turned on in response to output signal 122. At t2, the position monitor system status has returned to "NOT TRIGGERED" (e.g. due to the "EXIT" sensitivity setting having been selected and an occupant who had exited the bed at t1 returning to the bed at t2). As a result control signal 122 causes the light to revert, at t2, from on to off, i.e. to the operating condition it had been in at t0. Another example is seen in FIG. 6, example 2, event sequence t1, t2, t3 where the position monitor status has changed from "TRIGGERED" to "NOT TRIGGERED" at t2, and back to "TRIGGERED" at t3. At t2, the light, which had previously been on, has been turned off again (as it had been at t0) in response to output signal 122. At t3, the position monitor system status has returned to "TRIGGERED". As a result control signal 122 causes the light to revert, at t3, from off to on, i.e. to the operating condition it had been in at t1. This latter example is, of course, equivalent to the example in row A of FIG. 5A and in the event sequence t0 t1 of FIG. 6, example 2.

Figure 7:
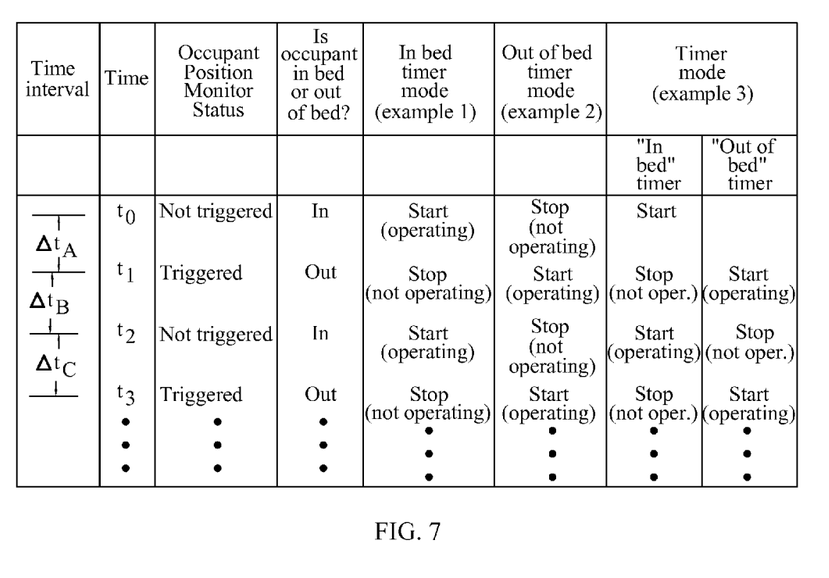
FIG. 7 is a table showing three examples of operation of time monitors as a function of the status of the position monitoring system.

FIG. 5A, in conjunction with FIG. 7, shows an example in which the nonalarm device is a time monitor such as a timer. In row A of FIG. 5A output signal 122 causes the timer to change its mode of operation. Assuming, for example, that the timer is one that keeps track of the time intervals during which the occupant is in the bed and was started at time t0 (FIG. 7, example 1), a change of position monitor status at t1 from "NOT TRIGGERED" to "TRIGGERED" causes the timer to change its mode of operation to STOP, i.e. the timer stops accumulating the lapse of time. Alternatively, if the timer is one that keeps track of the time intervals during which the occupant is out of the bed (FIG. 7 example 2, a change of position monitor status at t1 from "NOT TRIGGERED" to "TRIGGERED" causes the timer to change its mode of operation to START, i.e. the timer starts accumulating the lapse of time. Example 3 of FIG. 7 shows yet another variant in which the controller output signal affects two timers, one for measuring the accumulated time that the occupant is in the bed and another for measuring the accumulated time that the occupant is out of the bed.

Continuing to refer to FIG. 5A, row B shows the case where the occupant position monitor is in its armed, default state, the alarm is disabled, and the position monitor status is "NOT TRIGGERED". Under those conditions the alarm remains dormant. The mode of operation of the timer does not change. For example a timer for measuring the time that the occupant is in the bed continues operating; a timer for measuring the time that the occupant is out of the bed continues to not operate.

Row C of FIG. 5A, in conjunction with FIG. 7, shows how controller output signal 122 controls the timer or timers when the occupant position monitor status is "RESET". As before, the "RESET" status refers to a sequence of events in which the position monitor status changes from "TRIGGERED" to "NOT TRIGGERED", and back to "TRIGGERED" or vice versa ("NOT TRIGGERED" to "TRIGGERED", and back to "NOT TRIGGERED"). Considering only example 1 of FIG. 7, which example shows a timer for recording the amount of time the occupant is in the bed, the change of occupant position monitor status from "TRIGGERED" to "NOT TRIGGERED" at t2 causes the controller to change the mode of operation of the timer from "STOP" or not operating to "START" or operating. Similarly the change of occupant position monitor status from "NOT TRIGGERED" to "TRIGGERED" at t3 causes the controller to change the mode of operation of the timer from "START" or operating to "STOP" or not operating.

Rows D, E and F of FIG. 5A are similar to rows A, B and C respectively except that the alarm is enabled, as would be appropriate for an occupant whose movement or position needs to be restricted. As a result control signal 122 commands the alarm to become active (i.e. to issue whatever alarm stimulus the alarm is capable of) when the occupant position monitor status is "TRIGGERED". If the occupant position monitor status returns to "NOT TRIGGERED" the alarm, although still operational due to being enabled, is commanded to become inactive (i.e. to cease issuing the alarm stimulus). Alternatively the system could be arranged so that the alarm continues to issue the alarm stimulus.

Rows G through L of FIG. 5A are similar to rows A through F except that the occupant position monitor system is unarmed. As a result, the controller does not govern operation of either the alarm device or the nonalarm device irrespective of the status (enabled or disabled) of the alarm.

Figure 5B:
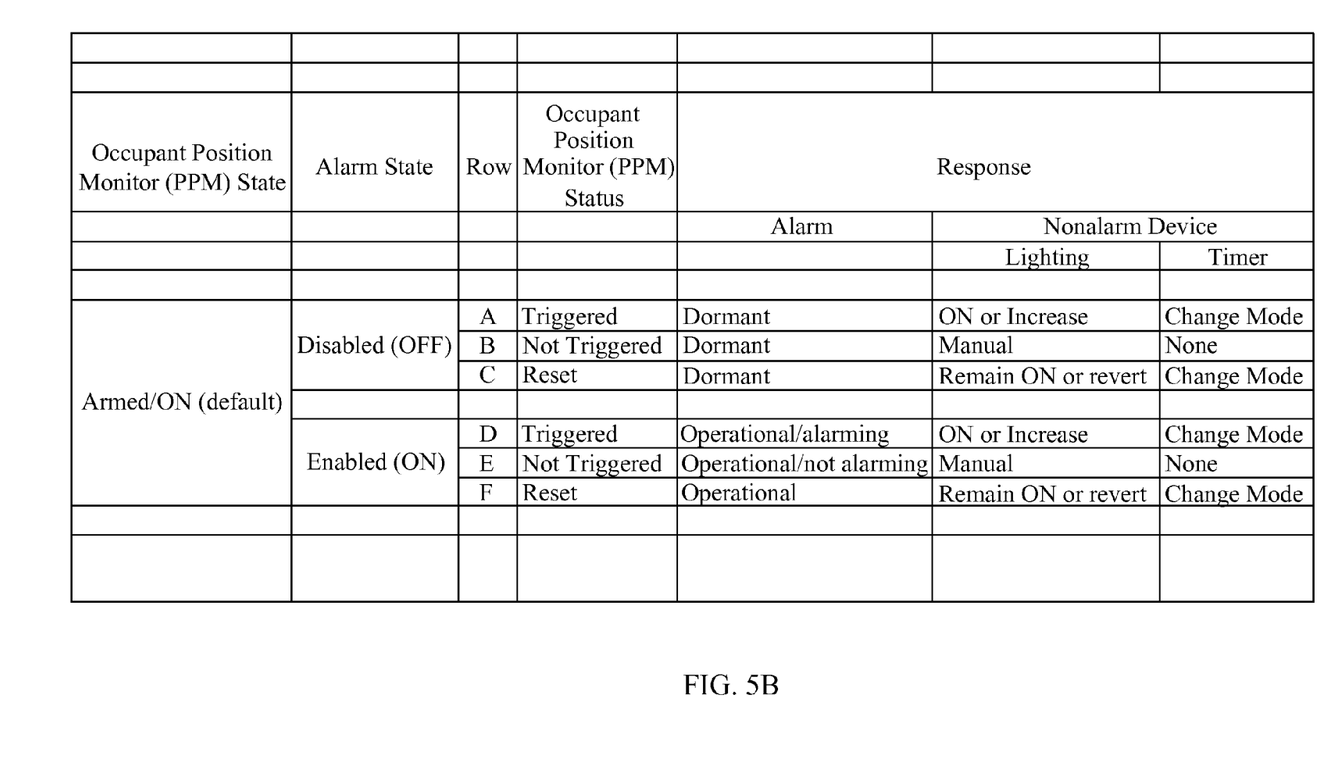
Figure 5C:
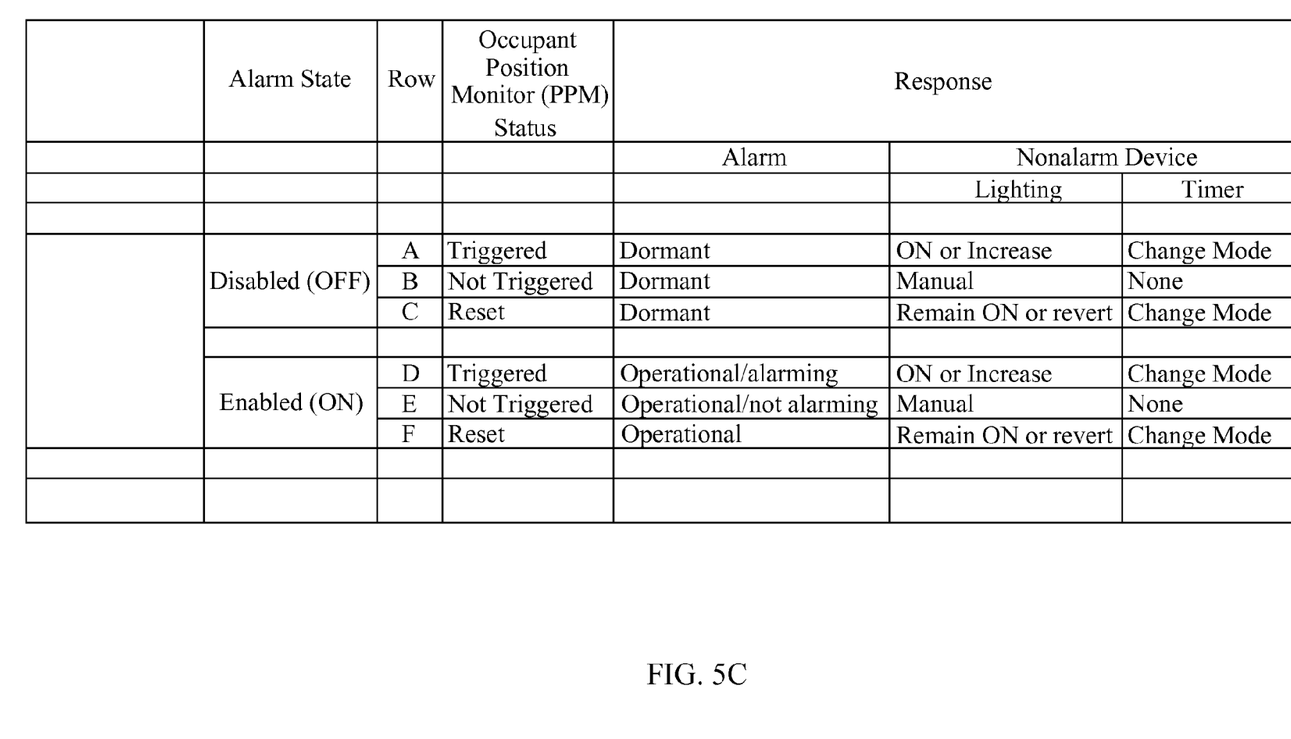

FIG. 5B is similar to FIG. 5A except that it explicitly accounts for the embodiment in which there is no state selector 104 for changing the state of the position monitoring system. As already noted, the position monitoring system in such an arrangement can be considered to be in an armed state by default or, as seen in FIG. 5C, the notion of the position monitoring system having any defined state associated with it can be disregarded.

Although the foregoing discussion uses a light and a timer as examples of nonalarm devices, other nonalarm devices could be used instead. With respect to the time monitor, system architectures other than that described above may be used may be used. In one option, elapsed time could be ascertained by a timer on the bed itself. In another option the controller output signal could be one that indicates only that an occupant has exited or entered the bed (or has violated or come into compliance with a positioning constraint associated with another sensitivity setting such as the PRE-EXIT or POSITION setting). External software such as software for a status board at a nurses' station, would receive the signal indicating that a patient had exited or entered a bed. The time stamp associated with these signals would be assigned by the external software which could also record the time stamps, carry out time related computations, and drive the display on the status board.

Figure 8:
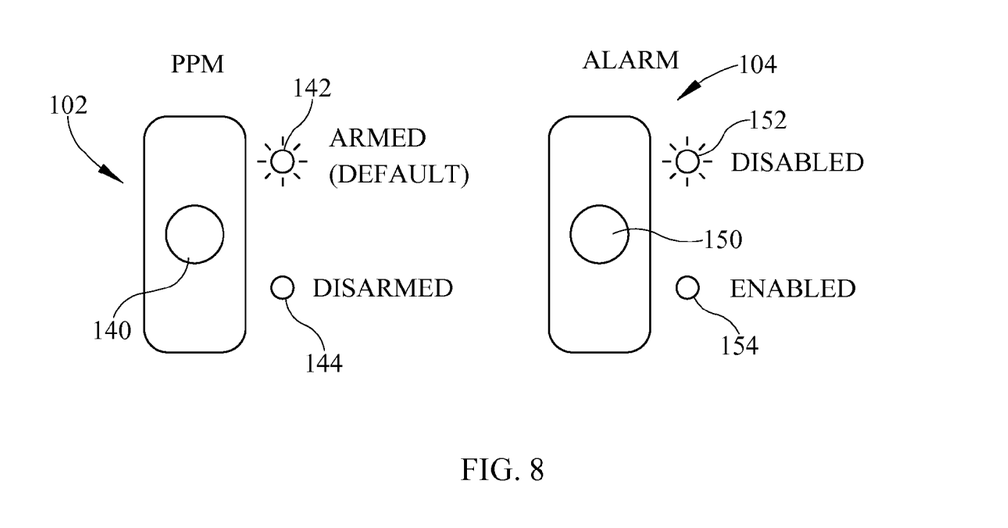
FIG. 8 is a view of one example of a user interface for an occupant position monitor state selector and an alarm device state selectors.

FIG. 8 shows one example of a user interface for state selectors 102, 104. The occupant position monitoring system state selector 104 includes a pushbutton 140 labelled "PPM", a first light 142, for example a light emitting diode (LED) labelled "ARMED", and a second LED 144 labelled "DISARMED". The first LED is depicted as illuminated to signify that the default state of the occupant position monitoring system is the armed state. By pressing button 140 a user can cycle between the armed and disarmed states. The existing state at any time is indicated by illumination of the corresponding LED. An alarm state selector 102 labelled "ALARM" includes a pushbutton 150 a third LED 152, labelled "DISABLED", and a fourth LED 154 labelled "ENABLED". The third light is depicted as illuminated to signify that the default state of the alarm is the enabled state. By pressing button 150 a user can cycle between the disabled and enabled alarm states. The existing state at any time is indicated by illumination of the corresponding LED. The circuitry for the LED's may be arranged so that if a user selects the disarmed state of the occupant position monitoring system, pushbutton 150 and LED's 152, 154 are rendered nonoperational until a user re-selects the armed state of the occupant position monitoring system, at which time the alarm 110 would be initialized in its default or disabled state.

Figure 9:
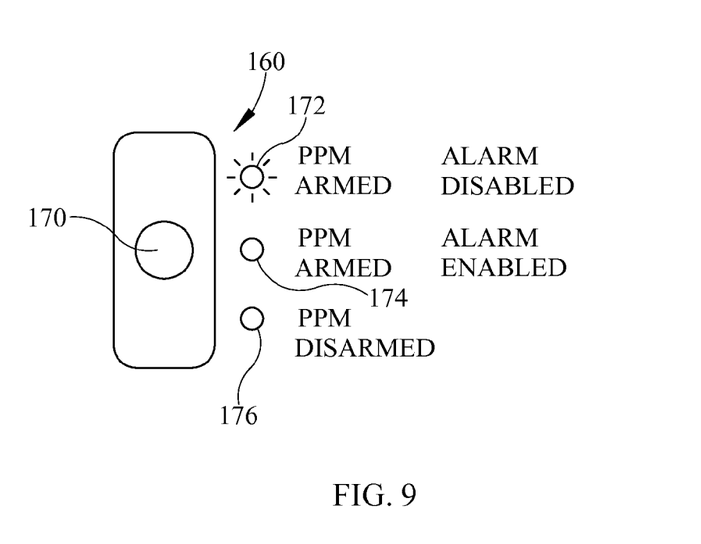
FIG. 9 is a view of an example integrated user interface for selecting occupant position monitor state and alarm state.

FIG. 9 shows an example arrangement in which the occupant position monitor state selector and the alarm state selector are accessed by way of an integrated user interface 160. The interface includes a pushbutton 170 and a triplet of LED's 172, 174, 176. By pressing button 170 a user can cycle between three states, a first state in which the occupant position monitoring system is armed and the alarm is disabled, a second state in which the occupant position monitoring system is armed and the alarm is enabled, and a third state in which the occupant position monitoring system is disarmed and therefore the state of the alarm is immaterial. The existing state at any time is indicated by illumination of the corresponding LED. The top-most light is depicted as illuminated to signify that the default state is the state in which the occupant position monitoring system is armed and the alarm is disabled.

User interfaces other than those shown in FIGS. 9-10 may be used. In one example a user interface from a conventional PPM system can be reconfigured to allow a user to change the state of the position monitoring system from the default, armed state to the disarmed state and vice versa (provided the system includes such an arm/disarm capability) and to enable or disable the alarm device. The interface need not be located on the bed itself but may be at a more remote location.

In the foregoing description the position monitoring system has an armed state and a disarmed state and the armed state is a default state. In another variant, the armed state is not necessarily the default state. The occupant support according to such a variant comprises an occupant support structure 32, a sensor such as first and or second sensors 50, 80 for producing a sensor output signal 52 as a function of occupant position, an alarm state selector 104 for enabling or disabling an alarm, and a position monitoring state selector 102 for changing the state of a position monitoring system between an armed state and a disarmed state. The occupant support also includes a controller 120 configured to receive the sensor output signal 52 and to produce a controller output signal 122 for commanding the alarm and a nonalarm device such that when the monitoring system is armed and the alarm is disabled the controller output signal governs operation of the nonalarm device but not operation of the alarm device and when the monitoring system is armed and the alarm is enabled the controller output signal governs operation of the nonalarm device and the alarm device.

Although this disclosure refers to specific embodiments, it will be understood by those skilled in the art that various changes in form and detail may be made without departing from the subject matter set forth in the accompanying claims.

I claim:

1. An occupant support comprising:
    an occupant support structure;
    an occupant position monitoring system comprising:
        a sensor for producing a sensor output signal as a function of occupant position on the occupant support structure;
        an alarm state selector for enabling or disabling an alarm;
        a controller configured to receive the sensor output signal and to produce a controller output signal for commanding the alarm and a nonalarm device such that:
    when the alarm is disabled the controller output signal governs operation of the nonalarm device but not operation of the alarm device and;
    when the alarm is enabled the controller output signal governs operation of the nonalarm device and the alarm device.

2. The occupant support of claim 1 including a position monitoring state selector for changing a state of the position monitoring system between an armed state and a disarmed state, the armed state being a default state, and wherein:
    when the monitoring system is armed and the alarm is disabled the controller output signal governs operation of the nonalarm device but not operation of the alarm device and;
    when the monitoring system is armed and the alarm is enabled the controller output signal governs operation of the nonalarm device and the alarm device.

3. The occupant support of claim 2 wherein when the monitoring system is disarmed the controller does not govern operation of the alarm and the nonalarm device.

4. The occupant support of claim 2 wherein the nonalarm device is a light, a time monitor or both and the controller output signal commands the alarm device and nonalarm device as set forth below:

| Alarm State | Occupant Position Monitor (PPM) State | Row | Occupant Position Monitor (PPM) Status | Alarm | Response Nonalarm Device Lighting | Timer |
|---|---|---|---|---|---|---|
| Disabled (OFF) | Armed/ON (default) | A | Triggered | Dormant | ON or Increase | Change Mode |
| | | B | Not Triggered | Dormant | Manual | None |
| | | C | Reset | Dormant | Remain ON or revert | Change Mode |
| Enabled (ON) | | D | Triggered | Operational/alarming | ON or Increase | Change Mode |
| | | E | Not Triggered | Operational/not alarming | Manual | None |
| | | F | Reset | Operational | Remain ON or revert | Change Mode |
| Disabled (OFF) | Not Armed/OFF | G | Triggered | Dormant | None | None |
| | | H | Not Triggered | Dormant | None | None |
| | | I | Reset | Dormant | None | None |
| Enabled (ON) | | J | Triggered | Dormant | None | None |
| | | K | Not Triggered | Dormant | None | None |
| | | L | Reset | Dormant | None | None | where the "Triggered" occupant monitor mode status indicates that occupant position relative to the occupant support is not within a prescribed limit, the "Not Triggered" occupant monitor mode status indicates that occupant position relative to the occupant support is within the prescribed limit, and the "Reset" occupant monitor mode status indicates that occupant position relative to the occupant support has reverted from not within the prescribed limit to within the prescribed limit or vice versa.

5. The occupant support of claim 2 wherein the nonalarm device is a light, a time monitor or both and the controller output signal commands the alarm device and nonalarm device as set forth below:

| Occupant Position Monitor (PPM) State | Alarm State | Row | Occupant Position Monitor (PPM) Status | Alarm | Response Nonalarm Device Lighting | Timer |
|---|---|---|---|---|---|---|
| Armed/ON (default) | Disabled (OFF) | A | Triggered | Dormant | ON or Increase | Change Mode |
| | | B | Not Triggered | Dormant | Manual | None |
| | | C | Reset | Dormant | Remain ON or revert | Change Mode |
| | Enabled (ON) | D | Triggered | Operational/alarming | ON or Increase | Change Mode |
| | | E | Not Triggered | Operational/not alarming | Manual | None |
| | | F | Reset | Operational | Remain ON or revert | Change Mode | where the "Triggered" occupant monitor mode status indicates that occupant position relative to the occupant support is not within a prescribed limit, the "Not Triggered" occupant monitor mode status indicates that occupant position relative to the occupant support is within the prescribed limit, and the "Reset" occupant monitor mode status indicates that occupant position relative to the occupant support has reverted from not within the prescribed limit to within the prescribed limit or vice versa.

6. The occupant support of claim 1 wherein the nonalarm device is a light, a time monitor or both and the controller output signal commands the alarm device and nonalarm device as set forth below:

| | Occupant | | Response | |
|---|---|---|---|---|
| | Position Monitor (PPM) | | Nonalarm Device | |
| Row | Status | Alarm | Lighting | Timer |
| A | Triggered | Dormant | ON or Increase | Change Mode |
| B | Not Triggered | Dormant | Manual | None |
| C | Reset | Dormant | Remain ON or revert | Change Mode |
| D | Triggered | Operational/ alarming | ON or Increase | Change Mode |
| E | Not Triggered | Operational/ not alarming | Manual | None |
| F | Reset | Operational | Remain ON or revert | Change Mode | where the "Triggered" occupant monitor mode status indicates that occupant position relative to the occupant support is not within a prescribed limit, the "Not Triggered" occupant monitor mode status indicates that occupant position relative to the occupant support is within the prescribed limit, and the "Reset" occupant monitor mode status indicates that occupant position relative to the occupant support has reverted from not within the prescribed limit to within the prescribed limit or vice versa.

7. The occupant support of claim 1 wherein the controller is configured to produce an EXITED output signal corresponding to an occupant having exited the occupant support and at least one other signal corresponding to the occupant having not exited the occupant support.

8. The occupant support of claim 7 wherein the at least one other signal comprises a PRE-EXIT signal corresponding to an occupant being in a position suggestive of an intent to exit the occupant support and a POSITION signal corresponding to an occupant being in an unsatisfactory or unauthorized position on the occupant support other than the position suggestive of an intent to exit the occupant support.

9. The occupant support of claim 1 wherein the nonalarm device is a light.

10. The occupant support of claim 1 wherein the nonalarm device is a time monitor.

11. The occupant support of claim 1 including a sensitivity selector for selecting among at least two occupant position monitoring sensitivity settings and wherein the controller output signal is a function of the sensitivity setting.

12. The occupant support of claim 1 including a sensitivity selector for selecting among exactly three occupant position monitoring sensitivity settings and wherein the controller output signal is a function of the sensitivity setting.

13. The occupant support of claim 1 including a sensitivity selector for selecting among three occupant position monitoring settings, an EXITED setting, a PRE-EXIT setting and a POSITION setting.

14. The occupant support of claim 13 wherein:
the EXITED setting, if selected, causes the occupant position monitoring system to be triggered if the controller perceives that the occupant has exited the occupant support;
the PRE-EXIT setting, if selected, causes the occupant position monitoring system to be triggered if the controller perceives that the occupant is in a position suggestive of an intent to exit the occupant support;
the POSITION setting if selected, causes the occupant position monitoring system to be triggered if the controller perceives that the occupant is in an unsatisfactory or unauthorized position other than the position suggestive of an intent to exit the occupant support.

15. The occupant support of claim 1 wherein the occupant position is responsive to changes in weight applied to the occupant support structure.

16. The occupant support of claim 1 wherein the occupant position is responsive to changes in position of the occupant on the occupant support structure.

17. An occupant support comprising:
an occupant support structure;
a sensor for producing a sensor output signal as a function of occupant position;
an occupant position monitoring system having an armed state and a disarmed state;
a position monitoring state selector for changing the state of the position monitoring system;
an alarm state selector for enabling or disabling an alarm;
a controller configured to receive the sensor output signal and to produce a controller output signal for commanding the alarm and a nonalarm device such that:
when the monitoring system is armed and the alarm is disabled the controller output signal governs operation of the nonalarm device but not operation of the alarm device and;
when the monitoring system is armed and the alarm is enabled the controller output signal governs operation of the nonalarm device and the alarm device.

18. The occupant support of claim 17 wherein the armed state of the position monitoring system is a default state.

* * * * *